United States Patent
Yuan et al.

(10) Patent No.: US 11,744,903 B2
(45) Date of Patent: Sep. 5, 2023

(54) METHOD FOR PREPARING CYCLODEXTRIN METAL ORGANIC FRAMEWORK (CD-MOF) STABLE IN AQUEOUS PHASE

(71) Applicant: Qilu University of Technology, Jinan (CN)

(72) Inventors: Chao Yuan, Jinan (CN); Bo Cui, Jinan (CN); Meng Zhao, Jinan (CN); Lu Lu, Jinan (CN); Jianpeng Li, Jinan (CN); Yaqi Liu, Jinan (CN)

(73) Assignee: Qilu University of Technology, Jinan (CN)

( * ) Notice: Subject to any disclaimer, the term of this patent is extended or adjusted under 35 U.S.C. 154(b) by 0 days.

(21) Appl. No.: 18/187,709

(22) Filed: Mar. 22, 2023

(65) Prior Publication Data
US 2023/0226216 A1    Jul. 20, 2023

(30) Foreign Application Priority Data
Mar. 23, 2022 (CN) .......................... 202210285661.8

(51) Int. Cl.
| | | |
|---|---|---|
| A61K 47/69 | (2017.01) | |
| A61K 31/352 | (2006.01) | |
| A61K 31/05 | (2006.01) | |
| A61K 31/343 | (2006.01) | |
| A61K 31/11 | (2006.01) | |

(52) U.S. Cl.
CPC .......... *A61K 47/6951* (2017.08); *A61K 31/05* (2013.01); *A61K 31/11* (2013.01); *A61K 31/343* (2013.01); *A61K 31/352* (2013.01)

(58) Field of Classification Search
CPC .................................................. A61K 47/6951
See application file for complete search history.

(56) References Cited

FOREIGN PATENT DOCUMENTS

| | | | |
|---|---|---|---|
| CN | 107550980 A | 1/2018 | |
| CN | 108671890 A | 10/2018 | |
| CN | 113444260 A | 9/2021 | |
| CN | 113750968 A | 12/2021 | |
| WO | WO-2009012551 A1 * | 1/2009 | ............... A23L 2/02 |

OTHER PUBLICATIONS

Vikramjeet Singh et al., "Moisture resistant and biofriendly CD-MOF nanoparticles obtained via cholesterol shielding", Chemical Communications, pp. 9246-9249.

* cited by examiner

*Primary Examiner* — James W Rogers

(57) ABSTRACT

A method for preparing a cyclodextrin metal organic framework (CD-MOF) stable in aqueous phase, including: dissolving β-cyclodextrin and solid potassium hydroxide in deionized water followed by magnetic stirring and ultrasonic treatment at room temperature, addition of methanol and stirring to obtain a reaction mixture; filtering the reaction mixture with a polytetrafluoroethylene membrane filter in a beaker; placing the beaker in methanol vapor to form a β-CD-MOF crystal; washing the β-CD-MOF crystal with ethanol followed by centrifugation and vacuum drying to obtain β-CD-MOF; preparing a β-CD-MOF-active substance complex by impregnation; and preparing an active substance-loaded β-CD-MOF-Tween 80 complex by physical adsorption modification followed by washing with anhydrous ethanol and vacuum drying.

4 Claims, 3 Drawing Sheets

METHOD FOR PREPARING CYCLODEXTRIN METAL ORGANIC FRAMEWORK (CD-MOF) STABLE IN AQUEOUS PHASE

CROSS-REFERENCE TO RELATED APPLICATIONS

This application claims the benefit of priority from Chinese Patent Application No. 202210285661.8, filed on Mar. 23, 2022. The content of the aforementioned application, including any intervening amendments thereto, is incorporated herein by reference in its entirety.

TECHNICAL FIELD

This application relates to biomaterials, and more particularly to a method for preparing a cyclodextrin metal organic framework (CD-MOF) stable in aqueous phase.

BACKGROUND

Currently, bioactive ingredients have attracted considerable attention. Some naturally-occurring active substances have unstable properties, such as poor water solubility, poor sensitivity to gastroenteric environment, and low in-vivo absorption rate, which greatly restrict their applications in food and medical industries. Therefore, it is imperative to improve the solubility of hydrophobic active substances and develop edible delivery systems for bioactive substances.

As a class of porous materials, metal organic frameworks (MOFs) are applicable to many technical fields including gas separation, immobilized enzymes, and sensors, due to their high porosity and large specific surface area. Generally, the MOFs are synthesized by a solvothermal method, which is generally performed by heating a mixture of metal salts and organic ligands in a solvent. Moreover, microwave, mechanochemistry, sonochemistry and electrochemistry techniques have also been applied to the MOF synthesis. However, the MOFs synthesized by the existing preparation methods cannot be recycled. Additionally, the use of highly-toxic components (such as metal ions and organic ligands) or chemical reagents in the synthesis greatly limit the applications of MOFs as a delivery carrier for edible substances in food industry. Thus, it is necessary to consider the bio-acceptability of metal ions and organic ligands. From this point, biocompatible metal ions, such as calcium (Ca), potassium (K), sodium (Na) ions, and biocompatible organic ligands, such as amino acids, carbohydrates, and cyclodextrin derivatives, are appreciated to promote the green production of MOFs, lower the safety risk, and improving the applicability in food industry.

Cyclodextrin metal organic frameworks (CD-MOFs) are characterized by excellent specific surface area and adjustable pore size. As a class of highly-porous supramolecular carriers, CD-MOFs have superior biocompatibility, and thus are considered as ideal candidate materials for the delivery of bioactive ingredients. The CD-MOFs are green and non-toxic materials constructed from biocompatible cyclodextrin as organic ligand and potassium ions as inorganic coupling unit. In consideration of the controllable self-assembly, large specific surface area and adjustable pore size, the CD-MOFs are suitable as carriers for active ingredients. Most of the existing CD-MOFs are unstable in water due to the weak coordination between metal ions and the organic ligand, and prone to quick structural collapse when exposed to moisture. The rapid water solubility of CD-MOFs limits their applications in food, medicine and other fields. Therefore, extensive efforts have been made to the design and development of a CD-MOF loaded with active ingredients which is capable of keeping stale in water. Currently, the water stability of CD-MOFs is enhanced mainly by modification with C60 coating, or processing into hydrogels through a cross-linking reaction. However, these methods struggle with excessive occupation of the cyclodextrin cavity by encapsulated substances, and time-consuming synthesis process. Consequently, it is urgently required to develop an effective method to improve the water stability of CD-MOFs to promote the utilization of bioactive substances, expanding the applications of the CD-MOFs in the food industry.

The non-toxic, highly-porous and biocompatible CD-MOFs are considered as an ideal encapsulating material, and can overcome the problem of poor solubility of natural active substances. By adopting an innovative method, the CD-MOF is coated with a non-ionic surfactant, and by means of the physical adsorption, the non-ionic surfactant coating plays a role as an outer shell to protect the inclusion complex from being exposed to water, expanding the applications of the CD-MOF-based inclusion complex under various aqueous conditions.

SUMMARY

An objective of this application is to provide a method for preparing a water-insoluble cyclodextrin metal organic framework (CD-MOF) to overcome the defects of poor water insolubility and low bioavailability of some active substances and instability of CD-MOF complex in water.

Technical solutions of this application are described as follows.

This application provides a method for preparing a cyclodextrin metal organic framework (CD-MOF) stable in aqueous phase, comprising:

(1) dissolving 0.4254 g of β-cyclodextrin and 0.168 g of solid potassium hydroxide in 15 mL of deionized water followed by magnetic stirring at room temperature for 30 min, ultrasonic treatment at room temperature for 10-15 min, and addition of 9 mL of methanol to obtain a reaction mixture; and stirring the reaction mixture for 5 min for uniform mixing;

(2) filtering the reaction mixture with a polytetrafluoroethylene (PTFE) membrane filter to collect a filtrate in a first beaker;

(3) placing the first beaker in methanol vapor to form a β-cyclodextrin metal organic framework (β-CD-MOF) crystal;

(4) washing the β-CD-MOF crystal 2-3 times with 10-15 mL of ethanol followed by centrifugation at 5000 rpm for 10 min;

(5) subjecting the β-CD-MOF crystal to vacuum drying at 40-60° C. for 24 h to remove solvent in channels of the β-CD-MOF crystal to obtain β-CD-MOF;

(6) preparing an inclusion complex of an active substance and the β-CD-MOF by impregnation;

(7) preparing a crude active substance-loaded β-CD-MOF-Tween 80 complex stable in aqueous phase by physical adsorption modification;

(8) washing the crude active substance-loaded β-CD-MOF-Tween 80 complex 2-3 times with 10-15 mL of anhydrous ethanol, followed by vacuum drying at 40-60° C. for 12 h to obtain a purified active substance-loaded β-CD-MOF-Tween 80 complex.

In an embodiment, the PTFE membrane filter has a pore size of 0.45 µm.

In an embodiment, step (3) comprises:

placing the first beaker in a second beaker containing 40-60 mL of methanol; wherein the second beaker is larger than the first beaker;

sealing the second beaker with a pressure-sensitive adhesive;

placing the second beaker in a magnetic field generator for 4 h; and placing the second beaker in an electrothermal constant-temperature circulating water bath at 40-60° C. for 12 h to slowly allow methanol to diffuse in the first beaker, and inducing a rapid nucleation by energy of magnetic field, so as to obtain the β-CD-MOF crystal.

In an embodiment, in step (6), the impregnation is performed through steps of:

ultrasonically dispersing 20 mg of the β-CD-MOF in 10 mL of anhydrous ethanol to obtain a β-CD-MOF solution; and adding a certain amount of the active substance to the β-CD-MOF solution, followed by stirring at 500 rpm for 1 h, and standing for 12 h to obtain the inclusion complex.

In an embodiment, the active substance is selected from the group consisting of glycitein, naringenin, cinnamic aldehyde, tanshinone IIA and resveratrol;

In an embodiment, in step (7), the physical adsorption modification method is performed through steps of:

adding 0.2-0.6 mL of Tween 80 to a freshly-prepared anhydrous ethanol solution containing the inclusion complex, followed by magnetic stirring at 80° C. for 30 min, cooling to room temperature and standing for 48 h to collect a precipitate as the crude active substance-loaded β-CD-MOF-Tween 80 complex.

Compared with the prior art, this application has the following beneficial effects.

(1) In this application, during the synthetic process, potassium ion is employed as a metal ion. Also, potassium ion is an essential element of human body and has desirable biocompatibility. Moreover, edible β-cyclodextrin with suitable pore size is employed as the organic ligand. The prepared β-cyclodextrin metal organic framework (β-CD-MOF) is fabricated by self-assembly through coordination bond between potassium ions and β-cyclodextrin. The materials used in the synthesis process have non-toxicity, safety, edibility and high biocompatibility, which avoids the usage of non-food-grade organic linkers and transition metal ions, solving the long-criticized problem caused by safety issues of MOFs.

(2) In this application, the magnetic field generator is used to prepare β-CD-MOF, which provides energy of the magnetic field to rapidly induce a generation of a crystal nuclei. In this way, the improved vapor diffusion method shortens the reaction time and obtains uniform crystals.

(3) The β-CD-MOF prepared herein has high specific surface area, good thermal stability and desirable porosity, which can be used as a carrier for the delivering active substances. The cyclodextrin metal organic frameworks loaded with active substances prepared by impregnation method does not change the inherent morphology of β-CD-MOF, solving the problems resulted from poor solubility and low bioavailability of some natural active substances in water. Moreover, cyclodextrin metal organic framework is green and degradable, which expands its applications in the fields of food, health products and pharmaceuticals.

(4) In this application, the cyclodextrin metal organic framework is used to embed the active substance. The physical adsorption between the hydroxyl of Tween 80 and the metal ion of β-CD-MOF allows the β-CD-MOF to be covered with a protective layer of Tween 80, effectively preventing water from entering the β-CD-MOF, and solving the problem of structure collapse of the cyclodextrin metal organic framework in water. The addition of Tween 80 further protects the stable existence of the active substance embedded in the cyclodextrin metal organic framework. The method provided herein provides a new way for constructing a water-stable metal organic framework loaded with bioactive substances.

DETAILED DESCRIPTION OF EMBODIMENTS

Figure 1:
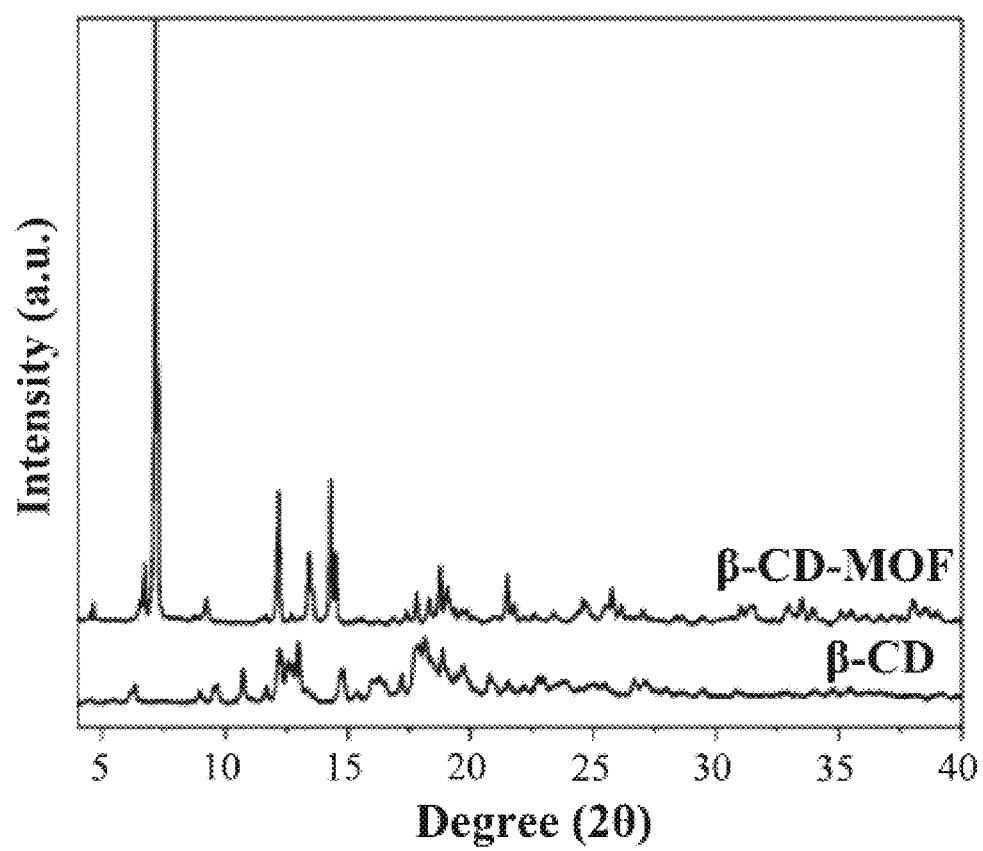
FIG. 1 shows an X-ray diffraction pattern of β-cyclodextrin (β-CD) and β-cyclodextrin metal organic framework (β-CD-MOF)

The technical solutions will be described in detail with reference to the following examples to facilitate the understanding of this application. It should be noted that these examples are not intended to limit this application.

Example 1 Preparation of Glycitein-Loaded β-Cyclodextrin Metal Organic Framework ((β-CD-MOF)-Tween 80 Complex (1) Reaction 0.4254 g of β-cyclodextrin and 0.168 g of solid potassium hydroxide were dissolved in 15 mL of deionized water. The reaction mixture was subjected to magnetic stirring at room temperature for 30 min, ultrasonic treatment at room temperature for 10 min, added with 9 mL of methanol, and stirred for 5 min for uniform mixing.

(2) Filtration

The reaction mixture was filtered with a 0.45 µm polytetrafluoroethylene (PTFE) membrane filter to collect a filtrate in a small beaker.

(3) Vapor Diffusion

The small beaker was placed in a large beaker containing 50 mL of methanol. The large beaker was sealed with a pressure-sensitive adhesive, and placed in a magnetic field generator for 4 h, and then placed in an electrothermal constant-temperature circulating water bath at 50° C. for 12 h, such that methanol slowly diffused into the small beaker, and the energy of the magnetic field induced rapid nucleation, so as to obtain a β-CD-MOF crystal.

(4) Washing

The β-CD-MOF crystal was washed twice with 10 mL of ethanol, and subjected to centrifugation at 5000 rpm for 10 min.

(5) Drying

The β-CD-MOF crystal obtained in step (4) was dried under vacuum at 50° C. for 24 h to remove solvent in channels to obtain β-CD-MOF.

(6) Preparation of an Inclusion Complex by Impregnation 20 mg of the β-CD-MOF was ultrasonically dispersed in 10 mL of anhydrous ethanol, to which 4.85 mg of glycitein was added. The reaction mixture was subjected to stirring at 500 rpm for 1 h, and standing for 12 h.

(7) Preparation of Glycitein-Loaded β-CD-MOF-Tween 80 Complex Stable in Aqueous Phase by Physical Adsorption Modification 0.5 mL of Tween 80 was added to a freshly-prepared anhydrous ethanol solution containing the inclusion complex of glycitein and β-CD-MOF. The reaction mixture was subjected to magnetic stirring at 80° C. for 30 min, rapid cooling to room temperature, and standing for 48 h to obtain a precipitate as the glycitein-loaded β-CD-MOF-Tween 80 complex.

(8) Washing

The precipitate was collected, washed twice with 10 mL of anhydrous ethanol, and transferred to another small beaker.

(9) Drying

The washed precipitate was dried under vacuum at 50° C. for 12 h to obtain a Tween 80-modified glycitein-loaded β-CD-MOF.

Example 2 Preparation of Naringenin-Loaded β-Cyclodextrin Metal Organic Framework (β-CD-MOF)-Tween 80 Complex (1) Reaction 0.4254 g of β-cyclodextrin and 0.168 g of solid potassium hydroxide were dissolved in 15 mL of deionized water. The reaction mixture was subjected to magnetic stirring at room temperature for 30 min, ultrasonic treatment at room temperature for 10 min, added with 9 mL of methanol, and stirred for 5 min for uniform mixing.

(2) Filtration

The reaction mixture was filtered with a 0.45 μm PTFE membrane filter to collect a filtrate in a small beaker.

(3) Vapor Diffusion

The small beaker was placed in a large beaker containing 50 mL of methanol. The large beaker was sealed with a pressure-sensitive adhesive, and placed in a magnetic field generator for 4 h, and then placed in an electrothermal constant-temperature circulating water bath at 50° C. for 12 h, such that methanol slowly diffused into the small beaker, and the energy of the magnetic field induced rapid nucleation, so as to obtain a β-CD-MOF crystal.

(4) Washing

The β-CD-MOF crystal was washed twice with 15 mL of ethanol, and subjected to centrifugation at 5000 rpm for 10 min.

(5) Drying

The β-CD-MOF crystal obtained in step (4) was vacuum dried at 60° C. for 24 h to remove solvent in channels to obtain β-CD-MOF.

(6) Preparation of an Inclusion Complex by Impregnation 20 mg of the β-CD-MOF was ultrasonically dispersed in 10 mL of anhydrous ethanol, to which 4.65 mg of naringenin was added. The reaction mixture was subjected to stirring at 500 rpm for 1 h, and standing for 12 h.

(7) Preparation of the Naringenin-Loaded β-CD-MOF-Tween 80 Complex Stable in Aqueous Phase by Physical Adsorption Modification 0.4 mL of Tween 80 was added to a freshly-prepared anhydrous ethanol solution containing the inclusion complex of naringenin and β-CD-MOF. The reaction mixture was subjected to magnetic stirring at 80° C. for 30 min, rapid cooling to room temperature, and standing for 48 h to obtain a precipitate as the naringenin-loaded β-CD-MOF-Tween 80 complex.

(8) Washing

The precipitate was collected, washed twice with 15 mL of anhydrous ethanol, and transferred to another small beaker.

(9) Drying

The washed precipitate was dried under vacuum at 50° C. for 12 h to obtain a Tween 80-modified naringenin-loaded β-CD-MOF.

Example 3 Preparation of Cinnamic Aldehyde-Loaded β-Cyclodextrin Metal Organic Framework (β-CD-MOF)-Tween 80 Complex (1) Reaction 0.4254 g of β-cyclodextrin and 0.168 g of solid potassium hydroxide were dissolved in 15 mL of deionized water. The reaction mixture was subjected to magnetic stirring at room temperature for 30 min, ultrasonic treatment at room temperature for 10 min, added with 9 mL of methanol, and stirred for 5 min for uniform mixing.

(2) Filtration

The reaction mixture was filtered through a 0.45 μm PTFE membrane filter to collect a filtrate in a small beaker.

(3) Vapor Diffusion

The small beaker was placed in a large beaker containing 45 mL of methanol. The large beaker was sealed with a pressure-sensitive adhesive, and placed in a magnetic field generator for 4 h, and then placed in an electrothermal constant-temperature circulating water bath at 50° C. for 12 h, such that methanol slowly diffused into the small beaker, and the energy of the magnetic field induced rapid nucleation, so as to obtain a β-CD-MOF crystal.

(4) Washing

The β-CD-MOF crystal was washed twice with 10 mL of ethanol, and subjected to centrifugation at 5000 rpm for 10 min.

(5) Drying

The β-CD-MOF crystal was dried under vacuum at 50° C. for 24 h to remove solvent in channels to obtain β-CD-MOF.

(6) Preparation of an Inclusion Complex by Impregnation 20 mg of β-CD-MOF was ultrasonically dispersed in 10 mL of anhydrous ethanol, to which 2.26 mg of cinnamic aldehyde was added, and subjected to stirring at 500 rpm for 1 h, and standing for 12 h.

(7) Preparation of the Cinnamic Aldehyde-Loaded β-CD-MOF-Tween 80 Complex Stable in Aqueous Phase by Physical Adsorption Modification 0.2 mL of Tween 80 was added to a freshly-prepared anhydrous ethanol solution containing the inclusion complex of cinnamic aldehyde and β-CD-MOF. The reaction mixture was subjected to magnetic stirring at 80° C. for 30 min, rapid cooling to room temperature, and standing for 48 h to obtain a precipitate as the cinnamic aldehyde-loaded β-CD-MOF-Tween 80 complex.

(8) Washing

The precipitate was collected, washed twice with 10 mL of anhydrous ethanol, and transferred to another small beaker.

(9) Drying

The washed precipitate was dried under vacuum at 60° C. for 12 h to obtain a Tween 80-modified cinnamic aldehyde-loaded β-CD-MOF.

Example 4 Preparation of Tanshinone IIA-Loaded β-Cyclodextrin Metal Organic Framework (β-CD-MOF)-Tween 80 Complex (1) Reaction 0.4254 g of β-cyclodextrin and 0.168 g of solid potassium hydroxide were dissolved in 15 mL of deionized water. The reaction mixture was subjected to magnetic stirring at room temperature for 30 min, ultrasonic treatment at room temperature for 15 min, added with 9 mL of methanol, and stirred for 5 min for uniform mixing.

(2) Filtration

The reaction solution was filtered through a 0.45 μm PTFE membrane filter to collect a filtrate in a small beaker.

(3) Vapor Diffusion

The small beaker was placed in a large beaker containing 60 mL of methanol. The large beaker was sealed with a pressure-sensitive adhesive, and placed in a magnetic field generator for 4 h, and then placed in an electrothermal constant-temperature circulating water bath at 40° C. for 12 h, such that methanol slowly diffused into the small beaker, and the energy of the magnetic field induced rapid nucleation, so as to obtain a β-CD-MOF crystal.

(4) Washing

The β-CD-MOF crystal was washed twice with 15 mL of ethanol, and subjected to centrifugation at 5000 rpm for 10 min.

(5) Drying

The β-CD-MOF crystal obtained in step (4) was dried under vacuum at 50° C. for 24 h to remove solvent in channels to obtain β-CD-MOF.

(6) Preparation of an Inclusion Complex by Impregnation 20 mg of β-CD-MOF was ultrasonically dispersed in 10 mL of anhydrous ethanol, to which 5.03 mg of tanshinone IIA was added, and subjected to stirring at a constant rate of 500 rpm for 1 h, and standing for 12 h.

(7) Preparation of the Tanshinone IIA-Loaded β-CD-MOF-Tween 80 Complex Stable in Aqueous Phase by Physical Adsorption Modification 0.5 mL of Tween 80 was added to a freshly-prepared anhydrous ethanol solution containing the inclusion complex of tanshinone IIA and β-CD-MOF. The reaction mixture was subjected to magnetic stirring at 80° C. for 30 min, rapid cooling to room temperature, and standing for 48 h to obtain a precipitate as the tanshinone IIA-loaded β-CD-MOF-Tween 80 complex.

(8) Washing

The precipitate was collected, washed twice with 15 mL of anhydrous ethanol, and transferred to another small beaker.

(9) Drying

The washed precipitate was dried under vacuum at 40° C. for 12 h to obtain a Tween 80-modified tanshinone IIA-loaded β-CD-MOF.

Example 5 Preparation of Resveratrol-Loaded β-Cyclodextrin Metal Organic Framework (β-CD-MOF)-Tween 80 Complex (1) Reaction 0.4254 g of β-cyclodextrin and 0.168 g of solid potassium hydroxide were dissolved in 15 mL of deionized water. The reaction mixture was subjected to magnetic stirring at room temperature for 30 min, ultrasonic treatment at room temperature for 15 min, added with 9 mL of methanol, and stirred for 5 min for uniform mixing.

(2) Filtration

The reaction mixture was filtered with a 0.45 μm PTFE membrane filter to collect a filtrate in a small beaker.

(3) Vapor Diffusion

The small beaker was placed in a large beaker containing 40 mL of methanol. The large beaker was sealed with a pressure-sensitive adhesive, and placed in a magnetic field generator for 4 h, and then placed in an electrothermal constant-temperature circulating water bath at 60° C. for 12 h, such that methanol slowly diffused into the large beaker, and the energy of the magnetic field induced rapid nucleation, so as to obtain a β-CD-MOF crystal.

(4) Washing

The β-CD-MOF crystal was washed twice with 10 mL of ethanol, and subjected to centrifugation at 5000 rpm for 10 min.

(5) Drying

The β-CD-MOF crystal obtained in step (4) was dried under vacuum at 55° C. for 24 h to remove solvent in channels to obtain β-CD-MOF.

(6) Preparation of an Inclusion Complex by Impregnation 20 mg of β-CD-MOF was ultrasonically dispersed in 10 mL of anhydrous ethanol, to which 3.90 mg of resveratrol was added, and subjected to stirring at 500 rpm for 1 h, and standing for 12 h.

(7) Preparation of the Resveratrol-Loaded β-CD-MOF-Tween 80 Complex Stable in Aqueous Phase by Physical Adsorption Modification 0.3 mL of Tween 80 was added to a freshly-prepared anhydrous ethanol solution containing the inclusion complex of resveratrol and β-CD-MOF. The reaction mixture was subjected to magnetic stirring at 80° C. for 30 min, rapid cooling to room temperature, and standing for 48 h to obtain a precipitate, as the resveratrol-loaded (3-CD-MOF-Tween 80 complex.

(8) Washing

The precipitate was collected, washed twice with 10 mL of anhydrous ethanol, and transferred to another small beaker.

(9) Drying

The washed precipitate was dried under vacuum at 50° C. for 12 h to obtain a Tween 80-modified resveratrol-loaded β-CD-MOF.

Characterization

FIG. 1 shows an X-ray diffraction pattern of 3-cyclodextrin (β-CD) and β-cyclodextrin metal organic framework (β-CD-MOF) according to an example of this application. As shown in FIG. 1, the X-ray diffraction pattern of β-CD-MOF was significantly different from that of β-CD. Compared with X-ray diffraction pattern of β-CD, many peaks in the X-ray diffraction pattern of β-CD-MOF slightly shifted, disappeared, or substituted by other sharper peaks. The characteristic peaks in the X-ray diffraction pattern of β-CD-MOF appeared at 4.62°, 6.70°, 7.14°, 9.22°, 12.16°, indicating that β-CD interacted with potassium ions ($K^+$) to form a more ordered crystal structure, which proves that the method provided herein successfully prepared β-CD-MOF.

Figure 2:
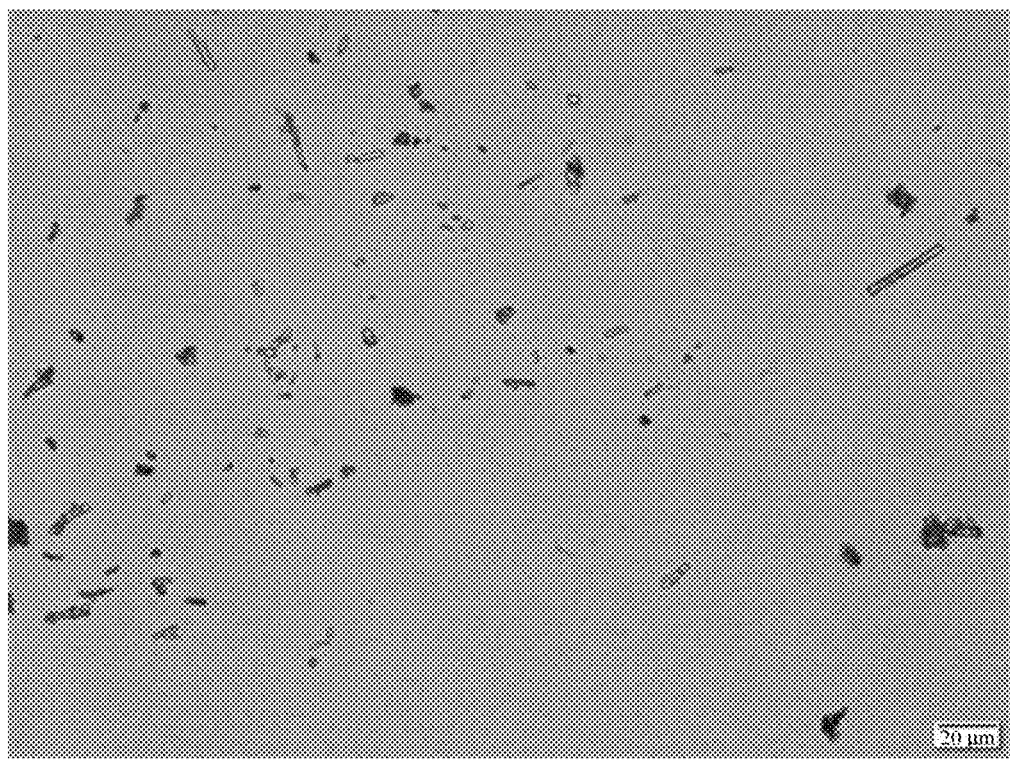
FIG. 2 is a microscopic morphology diagram of β-CD-MOF-Tween 80 prepared in Example 1 of this application.

FIG. 2 is a microscopic morphology diagram of β-CD-MOF-Tween 80 prepared in Example 1 of this application. As demonstrated in FIG. 2, most of the β-CD-MOFs exhibited darker color than the original transparent crystal due to the adsorption of Tween 80 on the surface, indicating that the β-CD-MOF was successfully modified by Tween 80 on the surface.

Figure 3:
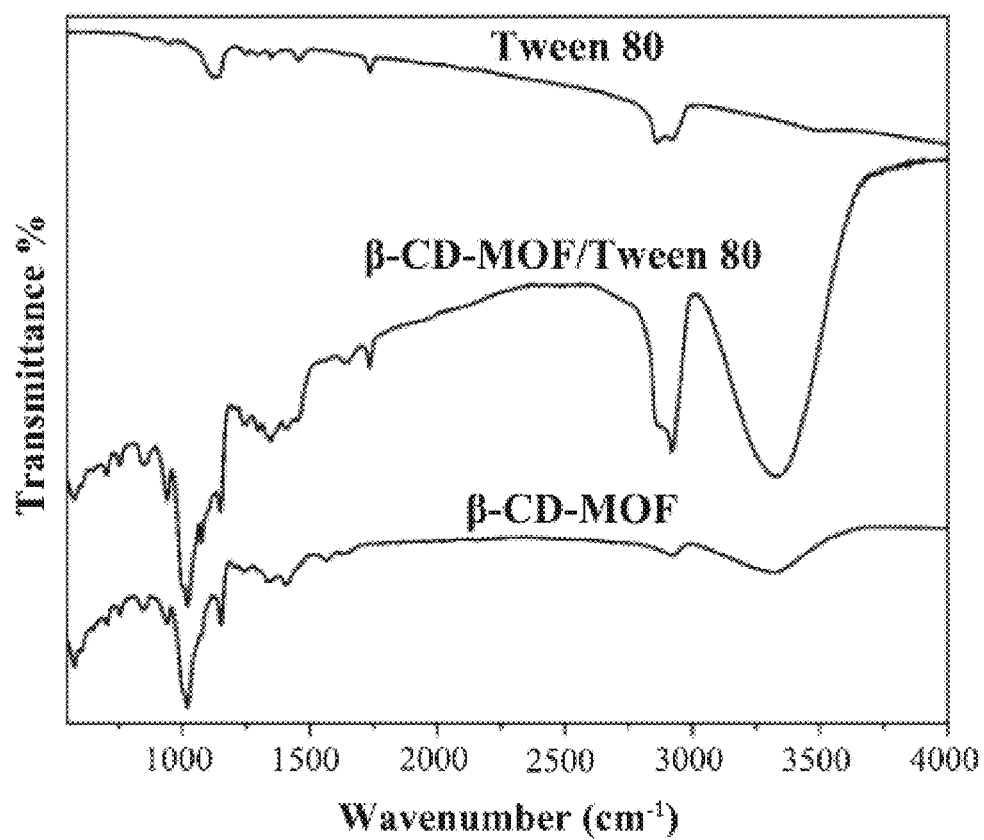
FIG. 3 is a Fourier transform infrared spectrum of the β-CD-MOF-Tween 80 complex prepared in Example 1 of this application.

FIG. 3 is a Fourier transform infrared spectrum of β-CD-MOF-Tween 80 complex prepared in Example 1 of this application. As shown in FIG. 3, the characteristic vibration peak of the double bond in Tween 80 appeared at 1735 cm$^{-1}$, indicating that Tween 80 successfully modified β-CD-MOF.

TABLE 1

Encapsulation rates of β-CD-MOF for different active substances

| Carrier | Active substances | Encapsulation rate |
| --- | --- | --- |
| β-CD-MOF | Glycitein | 76.34 ± 0.23% |
| β-CD-MOF | Naringenin | 70.23 ± 0.15% |
| β-CD-MOF | Cinnamic aldehyde | 79.68 ± 0.28% |
| β-CD-MOF | Tanshinone IIA | 76.40 ± 0.67% |
| β-CD-MOF | Resveratrol | 82.19 ± 0.35% |

Table 1 demonstrated encapsulation rates of β-CD-MOFs loaded with different active substances prepared in Examples 1-5. It can be seen from Table 1 that β-CD-MOF could achieve higher encapsulation rates for different active substances. Due to the porous network structure, β-CD-MOF is an excellent carrier for some hydrophobic active substances, which can exert the advantages of MOF in the delivery of functional active substances.

TABLE 2

Changes in structure retention rate of β-CD-MOF and β-CD-MOF-Tween 80 complex

| Samples | 1d | 2d | 3d | 4d | 5d |
| --- | --- | --- | --- | --- | --- |
| β-CD-MOF | 34.25 ± 1.12% | 17.78 ± 2.38% | 5.66 ± 1.23% | 1.78 ± 0.16% | 0.58 ± 0.45% |
| β-CD-MOF-Tween 80 complex | 100.00 ± 0.00% | 98.50 ± 1.32% | 98.12 ± 0.76% | 97.82 ± 1.43% | 97.28 ± 0.45% |

Table 2 shows the changes in the structure retention rates for β-CD-MOF and 13-CD-MOF-Tween 80 complex under a treatment at a constant temperature of 25° C. and high humidity of 90% within 5 days. It can be illustrated from Table 2 that the structure of β-CD-MOF completely collapsed after 5-day exposure to high humidity environment. After the same humidity treatment, the structure of β-CD-MOF-Tween 80 complex did not notably change. Therefore, Tween 80 on the surface, as the hydrophobic protective layer, effectively protected β-CD-MOF from water molecules, so as to ensure the integrity of MOF.

TABLE 3

Changes in moisture absorption rates of β-CD-MOF and β-CD-MOF-Tween 80 complex over time

| Samples | 1d | 2d | 3d | 4d | 5d | 6d | 7d | 8d |
| --- | --- | --- | --- | --- | --- | --- | --- | --- |
| β-CD-MOF | 23.22 ± 1.56% | 23.50 ± 0.44% | 22.67 ± 0.21% | 21.75 ± 1.61% | 22.25± 0.45% | 22.45 ± 0.43% | 23.56 ± 1.50% | 23.38 ± 0.48% |
| β-CD-MOF-Tween 80 complex | 1.15 ± 0.28% | 2.56 ± 0.13% | 4.71 ± 0.88% | 5.44 ± 1.12% | 8.89 ± 1.76% | 10.22 ± 0.98% | 15.77 ± 1.71% | 19.26 ± 1.43% |

Table 3 demonstrated the change in moisture absorption rates of β-CD-MOF and β-CD-MOF/Tween 80 complex under certain conditions. A certain amount of β-CD-MOF and β-CD-MOF/Tween 80 complex were weighed and placed in a chamber with constant temperature at 25° C. and humidity of 90%. After a certain time, the sample was taken out and weighed to calculate the moisture absorption rate. As illustrated in Table 3, the β-CD-MOF crystal reached a maximum moisture absorption rate of 23% within 1 day, while the β-CD-MOF/Tween 80 complex reached a maximum moisture absorption rate of only 19% after being exposed to a high humidity environment for 8 days indicating that the modification by Tween 80 could slow down the water absorption and enhance the water stability of the β-CD-MOF.

What is claimed is:

1. A method for preparing a cyclodextrin metal organic framework (CD-MOF) stable in aqueous phase, comprising:
   (1) dissolving 0.4254 g of β-cyclodextrin and 0.168 g of solid potassium hydroxide in 15 mL of deionized water followed by magnetic stirring at room temperature for 30 min, ultrasonic treatment at room temperature for 10-15 min, and addition of 9 mL of methanol to obtain a reaction mixture; and stirring the reaction mixture for 5 min for uniform mixing;
   (2) filtering the reaction mixture with a polytetrafluoroethylene (PTFE) membrane filter to collect a filtrate in a first beaker;
   (3) placing the first beaker in methanol vapor to form a β-cyclodextrin metal organic framework (β-CD-MOF) crystal;
   (4) washing the β-CD-MOF crystal 2-3 times with 10-15 mL of ethanol followed by centrifugation at 5000 rpm for 10 min;
   (5) subjecting the β-CD-MOF crystal to vacuum drying at 40-60° C. for 24 h to remove solvent in channels of the β-CD-MOF crystal to obtain β-CD-MOF;
   (6) preparing an inclusion complex of an active substance and the β-CD-MOF by impregnation; wherein the active substance is selected from the group consisting of glycitein, naringenin, cinnamaldehyde, tanshinone IIA and resveratrol;
   (7) preparing a crude active substance-loaded β-CD-MOF-Tween 80 complex stable in aqueous phase by physical adsorption modification;
   wherein the physical adsorption modification is performed through steps of:
   adding 0.2-0.6 mL of Tween 80 to a freshly-prepared anhydrous ethanol solution containing the inclusion complex followed by magnetic stirring at 80° C. for 30 min, cooling to room temperature and standing for 48 h to collect a precipitate as the crude active substance-loaded β-CD-MOF-Tween 80 complex;
   (8) washing the crude active substance-loaded β-CD-MOF-Tween 80 complex 2-3 times with 10-15 mL of anhydrous ethanol followed by vacuum drying at 40-60° C. for 12 h to obtain a purified active substance-loaded β-CD-MOF-Tween 80 complex.

2. The method of claim 1, wherein the PTFE membrane filter has a pore size of 0.45 μm.

3. The method of claim 1, wherein step (3) comprises:
placing the first beaker in a second beaker containing 40-60 mL of methanol; wherein the second beaker is larger than the first beaker;
sealing the second beaker with a pressure-sensitive adhesive;
placing the second beaker in a magnetic field generator for 4 h; and
placing the second beaker in an electrothermal constant-temperature circulating water bath at 40-60° C. for 12 h to allow methanol to diffuse into the first beaker to obtain the β-CD-MOF crystal.

4. The method of claim 1, wherein in step (6), the impregnation is performed through steps of:
ultrasonically dispersing 20 mg of the β-CD-MOF in 10 mL of anhydrous ethanol to obtain a β-CD-MOF solution; and adding a certain amount of the active substance to the β-CD-MOF solution, followed by stirring at 500 rpm for 1 h and standing for 12 h to obtain the inclusion complex.

* * * * *